United States Patent [19]
Morrow

[11] 4,129,479
[45] Dec. 12, 1978

[54] METHOD OF ANALYZING RESIDUAL CHLORINE

[75] Inventor: James J. Morrow, Norristown, Pa.

[73] Assignee: Fischer & Porter Co., Warminster, Pa.

[21] Appl. No.: 545,515

[22] Filed: Jan. 30, 1975

Related U.S. Application Data

[63] Continuation of Ser. No. 313,644, Dec. 11, 1972, abandoned.

[51] Int. Cl.² ............................................. G01N 27/46
[52] U.S. Cl. .................................. 204/1 T; 204/195 R
[58] Field of Search ..................... 204/1 T, 195 R, 1 B

[56] References Cited

U.S. PATENT DOCUMENTS

| | | | |
|---|---|---|---|
| 2,350,378 | 6/1944 | Wallace | 204/195 R |
| 2,370,871 | 3/1945 | Marks | 204/195 R |
| 2,414,411 | 1/1947 | Marks | 204/195 R |
| 3,413,199 | 11/1968 | Morrow | 204/1 T |

OTHER PUBLICATIONS

"Analytical Chemistry", vol. 19, No. 3, Mar., 1947, pp. 200–204.

Primary Examiner—T. Tung
Attorney, Agent, or Firm—Michael Ebert

[57] ABSTRACT

A continuous analyzer for accurately measuring the free chlorine residual in a chlorinated water supply having an ammonia content which gives rise to a combined chlorine residual whose bactericidal effectiveness is poor as compared to free chlorine. The analyzer includes an amperometric cell through which a sample from the supply is conducted, the cell being provided with a measuring electrode and a counter electrode. Connected in series with the electrodes is an external voltage source whose level is set to impress a potential on the measuring electrode at which the current flow in the cell as a result of the chlorine content of the sample increases progressively in accordance with the concentration of free chlorine residual, the cell being essentially insensitive to combined chlorine residual.

2 Claims, 9 Drawing Figures

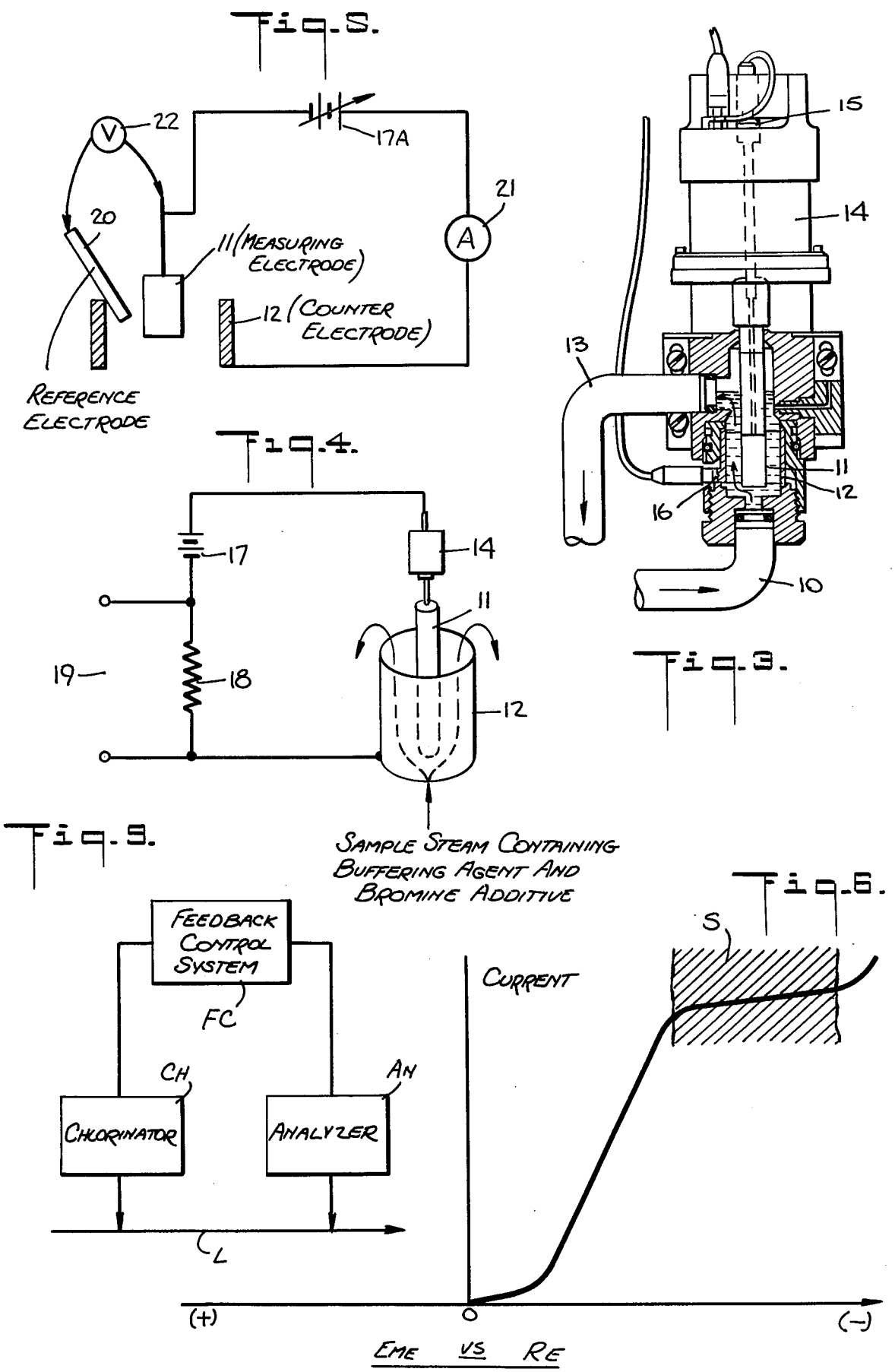

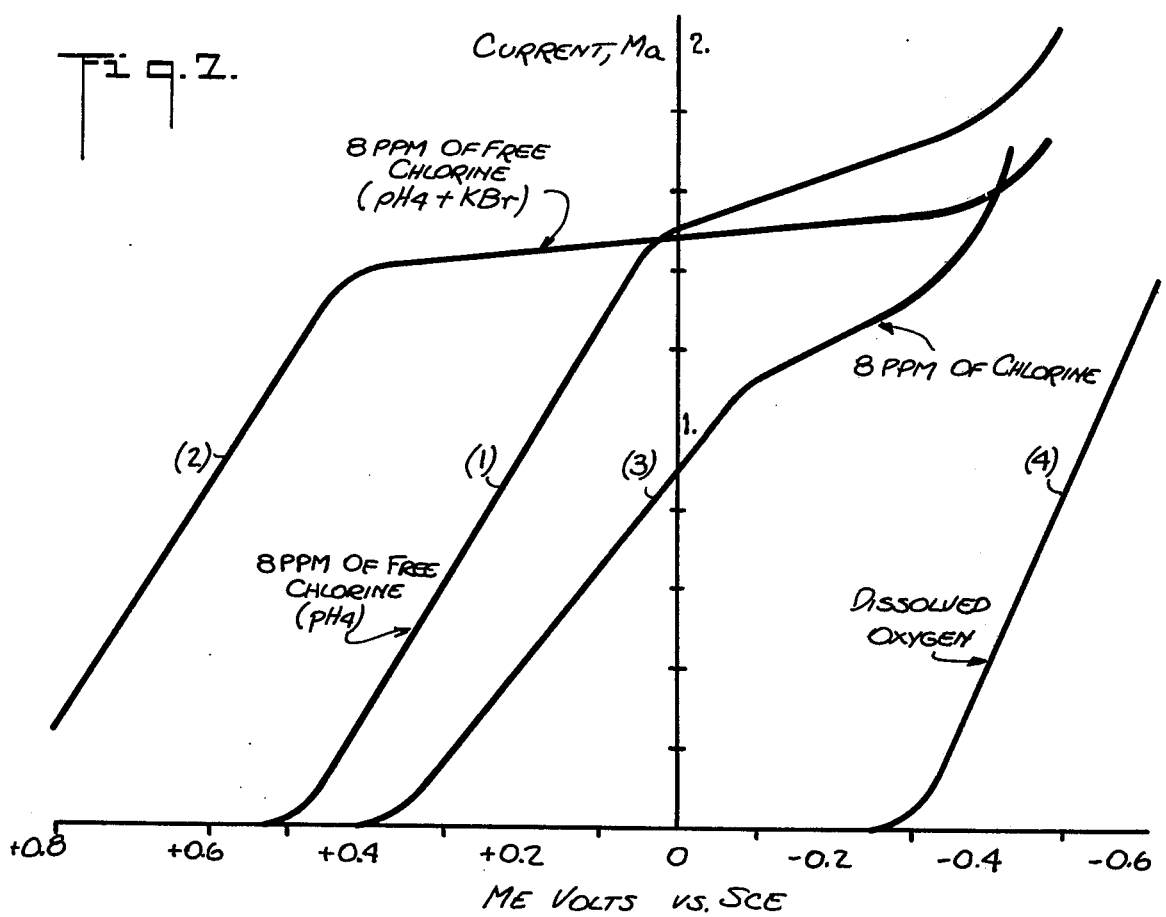
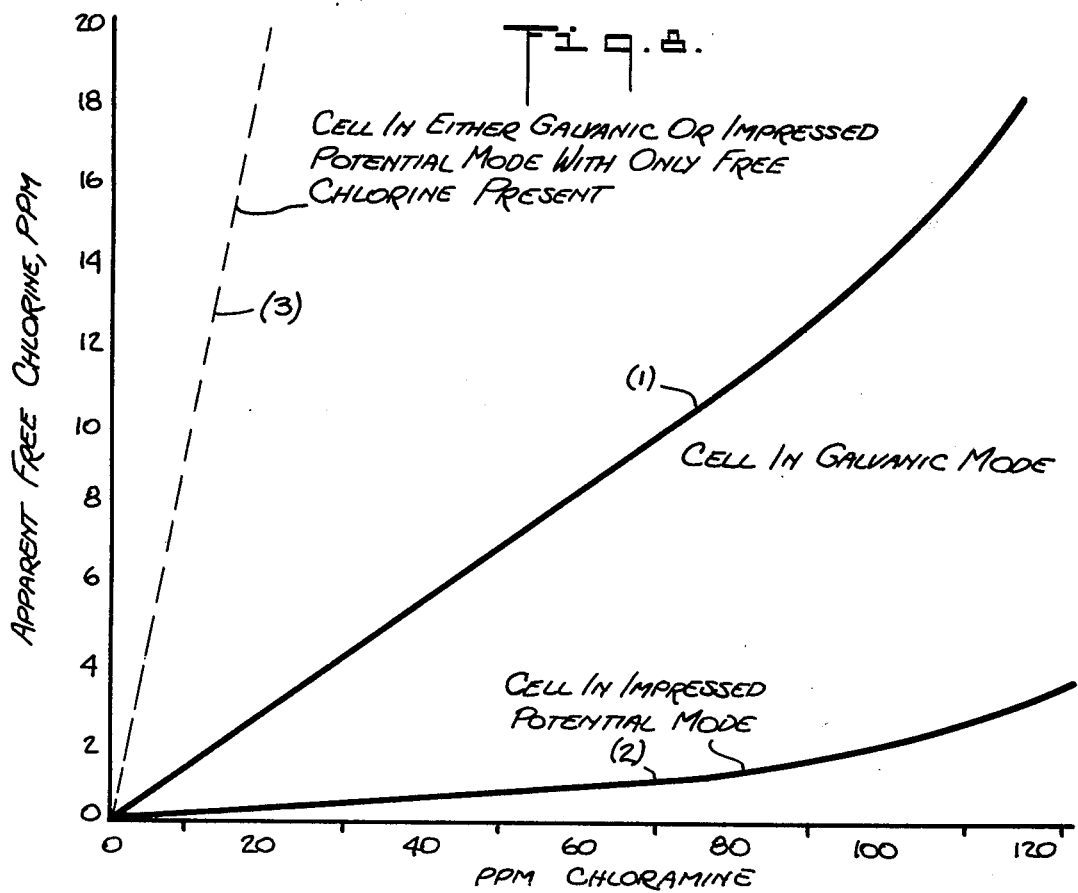

METHOD OF ANALYZING RESIDUAL CHLORINE

RELATED APPLICATION

This application is a continuation of application Ser. No. 313,644, filed Dec. 11, 1972, now abandoned.

BACKGROUND OF THE INVENTION

This invention relates generally to chlorine analysis, and more particularly to the amperometric measurement of free chlorine residual.

Chlorination is widely used to purify water supplies. In practice, chlorine is introduced at a selected point in the water supply system, and flow then takes place into a tank or through a region of flow which is sufficient for the chlorine to act effectively on the contaminants present in the water to produce a disinfecting action. In order to determine whether the amount of chlorine present is adequate to effect disinfection, measurements are made beyond the chlorine input point. The measurement output signal may also serve to regulate the feed of chlorine into the system to insure that the amount is adequate but not excessive.

The amount of chlorine added to the water is referred to as the "dosage," and is usually expressed as parts per million (ppm). The amount of chlorine used up or consumed by bacteria, algae, organic compounds and some inorganic substances, such as iron or manganese, is designated as the "demand." Since many of the reactions with chlorine are not instantaneous, but require time to reach completion, chlorine demand is time-dependent.

The amount of chlorine remaining in the water at the time of measurement is referred to as the "residual." Residual is therefore determined by the dosage subtracted from the demand. Inasmuch as chlorine demand is time-dependent, this dependency is likewise true of chlorine residual.

When chlorine dissolves in water, a mixture of hypochlorous and hydrochloric acids is formed. Actually, the hydrochloric acid always completely dissociates into hydrogen and chloride ions, whereas the hypochlorous acid only partially dissociates into hydrogen and hypochlorite ions. In either the hypochlorous acid or hypochlorite ion form, chlorine is called "free chlorine residual." Free chlorine residual has a highly effective killing power toward bacteria.

Should the chlorinated water contain ammonia or certain amino (nitrogen-based) compounds, as is the case with sewage, then addition compounds, called chloramines, are formed. Chloramines occur almost instantaneously, and though several reactions are possible between hypochlorous acid and ammonia, chloramines collectively are referred to as "combined chlorine residual." This combined chlorine residual has a much lower bactericidal effect than free chlorine residual.

When sufficiently high chlorine dosages are applied to waters containing ammonia, different reactions will occur, resulting in the destruction of the ammonia and the formation of free chlorine residual. Thus, for water containing a known amount of ammonia, if one starts with a chlorine dosage which is low, chloramines will be formed resulting in a combined chlorine residual whose bactericidal effect is relatively weak. And as the dosage is raised, the amount of combined chlorine residual produced also increases, until a peak is reached when all of the free ammonia is used up in the formation of chloramine. And as the dosage is elevated beyond the level at which the combined chlorine residual peaks, destruction of the chloramines, which are unstable, takes place until a breakpoint is reached indicating that chloramine destruction is at its maximum. At breakpoint, the first appearance of free chlorine occurs.

A further increase in chlorine dosage beyond this breakpoint results in the formation of free chlorine residual. Thus by using a chlorine dosage sufficient to attain the breakpoint state, one is able to get rid of virtually all ammonia and a majority of chloramines. It is to be noted that complete destruction of chloramines seldom occurs at breakpoint, and some chloramines invariably persist in the presence of free chlorine.

Domestic waste water is typically high in ammonia, the ammonia resulting primarily from hydrolysis of urea. Normally, almost all of the nitrogen formed in solutions that enter a waste treatment plant are in the least oxidized, ammonia form. In conventional secondary waste treatment, a portion of the ammonia will be completely nitrified to nitrate, some will be only partially nitrified to nitrite and a portion will remain as ammonia.

Although some nitrogen is removed from domestic waste water by means of secondary treatment, the percentage of removal is usually only twenty to fifty percent. The remaining nitrogen is discharged from the treatment system into a receiving body of water with adverse ecological results, for nitrogen discharged as ammonia or nitrite exhibits an oxygen demand on the receiving body and creates a chlorine demand at downstream water-treatment plants. Moreover, the nitrate form contributes significantly to eutrophication or algae bloom in streams and lakes.

As pointed out previously, chlorination of sewage plant effluents in the presence of ammonia gives rise to chloramines, which is a far less effective disinfectant than free chlorine. Breakpoint chlorination has therefore been used to destroy ammonia, but it has not heretofore been possible to adequately control the technique involved.

The obvious way to govern the process is to use conventional feedback control means based on free chlorine residual, for the breakpoint at which ammonia destruction is optimized, is characterized by the first appearance of a free residual. But to utilize this approach, an analytical method must exist that is capable of accurately and continuously measuring free chlorine in the presence of substantial combined chlorine residual. Furthermore, it is of the utmost importance, should only combined chlorine residual be present, which is indicative that breakpoint has yet to be reached, that the continuous analyzer then indicate that essentially no free chlorine is present.

Existing amperometric cells used for the measurement of free chlorine residual are also responsive to combined chlorine residual (albeit less sensitive) and therefore produce a misleading reading of apparent free chlorine, thereby making effective breakpoint control difficult to accomplish.

SUMMARY OF THE INVENTION

In view of the foregoing, the main object of this invention is to provide a continuous analyzer for accurately measuring the free chlorine residual in a sample also containing substantial quantities of combined chlorine residual.

Because an analyzer in accordance with the invention does not falsely read an apparent free chlorine residual arising from chloramine interference, it makes possible the exact detection of the breakpoint indicating that a chlorine dosage has been reached at which all ammonia compounds have been destroyed, whereby a further increase in dosage results in the formation of free chlorine residual. Thus one salient feature of the invention is that it lends itself to the control of chlorine dosage so as to optimize the destruction of ammonia compounds.

More specifically, it is an object of this invention to provide a continuous analyzer of the amperometric type, wherein the electrode cell operates in the impressed-potential mode to indicate the amount of free chlorine residual to the exclusion of combined chlorine error.

Briefly stated, these objects are attained in an amperometric cell having a measuring electrode and a counter electrode which, together, define a passage through which a sample stream is caused to flow at a controlled rate. Connected in series with the electrodes and a load resistance is an external voltage source whose level is set to impress on the measuring electrode a potential at which the current flow through the cell produces a voltage across the load resistor which is linearly related to the level of free chlorine residual in the sample, but is insensitive to the level of combined chlorine residual therein.

Thus by deriving a sample of liquid from a wastewater line to which a standard chlorinator is coupled, and feeding the sample to an impressed-potential analyzer in accordance with the invention, the analyzer signal yielded at breakpoint representing the point at which the combined chlorine residual drops to its minimal level and free chlorine residual is formed. This signal may be fed to a feedback control means coupled to the chlorinator to govern the dosage so as to optimize its effect, whereby ammonia is destroyed and the deleterious consequences resulting from the presence of ammonia in the receiving waters is avoided.

OUTLINE OF THE DRAWING

For a better understanding of the invention, as well as other objects and further features thereof, reference is made to the following detailed disclosure to be read in conjunction with the accompanying drawings, wherein:

FIG. 3 illustrates schematically the structure of an impressed-potential amperometric cell in accordance with the invention;

FIG. 4 is the circuit of the cell shown in FIG. 3;

FIG. 5 illustrates the test circuit for determining the proper value of impressed potential;

FIG. 6 is a curve representing the operation of the circuit of FIG. 5;

FIG. 7 shows a series of current-voltage curves illustrative of the principles underlying the invention;

FIG. 8 shows curves which compare the behavior of a conventional galvanic cell with an impressed-potential cell in accordance with the invention; and FIG. 9 is a chlorinated water-supply system which includes a continuous analyzer in accordance with the invention to carry out breakpoint control.

DESCRIPTION OF THE INVENTION

Figure 1:
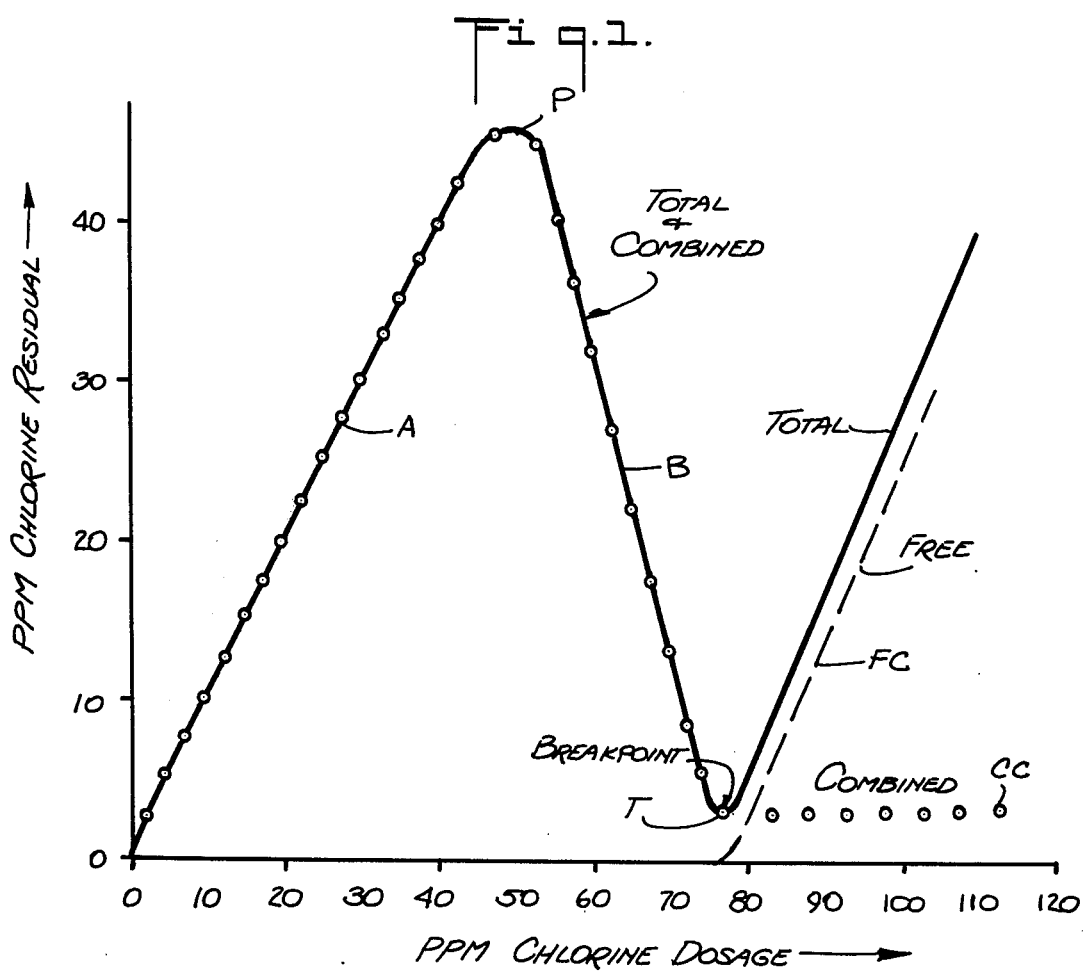
FIG. 1 is a typical breakpoint curve of a sewage effluent.

Reference is now made to FIG. 1, which shows in somewhat idealized form, the breakpoint curve that is typical of a sewage effluent containing 10 ppm ammonia residual.

Low chlorine dosages result in the formation of mono and dichloramine, and are depicted as increasing residual on the left end (A) of the curve. The peak (P) of the curve occurs when all of the free ammonia is used up, forming chloramine. With excess chlorine due to higher dosages, the chloramines are unstable, and destruction occurs due to one or both of the following reactions:

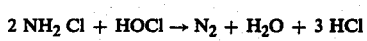

$2 NH_2Cl + HOCl \rightarrow N_2 + H_2O + 3 HCl$

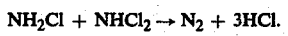

$NH_2Cl + NHCl_2 \rightarrow N_2 + 3HCl.$

This reaction accounts for the downwardly-sloping portion (B) of the curve on the right side of peak (P). When the chlorine dosage reaches approximately eight to ten times the ammonia concentration (the theoretical ratio is 7.6, but side reactions also occur), the "breakpoint" or trough (T) of the curve is reached, indicating that all the ammonia compounds have been destroyed. Further increase in chlorine dosage results in the formation of free chlorine residual.

In FIG. 1, it will be seen that the breakpoint T takes place at a chlorine dosage of 76 ppm in a sewage effluent containing 10 ppm of ammonia; hence it occurs at the theoretical 7.6 ratio. It will be noted that a combined chlorine (CC) residual of about 3 ppm exists past breakpoint, whereas as the chlorine dosage is increased beyond 76 ppm, the free chlorine (FC) residual rises sharply.

It will be evident that if the ammonia concentration remained steady at 10 ppm, the process could be very easily controlled, based on a 3 ppm free chlorine residual, which would correspond to a chlorine dosage of 79 ppm. But as a practical matter, the ammonia concentration does not remain at a steady level and this creates certain problems, as will later become evident.

Figure 2:
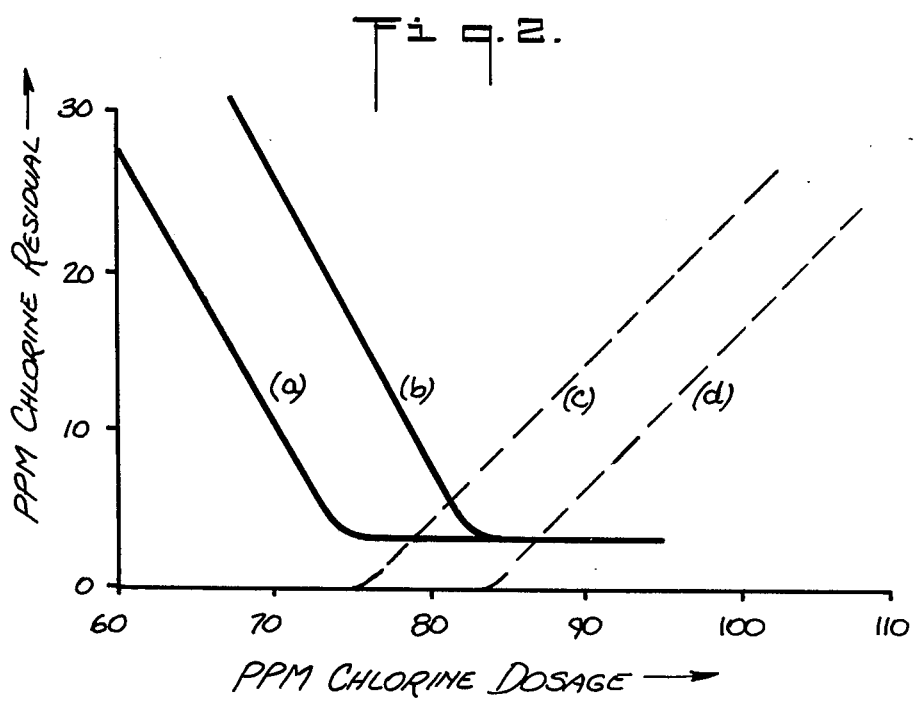
FIG. 2 shows curves, in the vicinity of breakpoint, representing combined chlorine residual and free chlorine residual at different ammonia levels.

Referring now to FIG. 2, the curves (a) and (c) show the combined chlorine residual and free chlorine residual values, respectively, these corresponding to an initial ammonia level of 10 ppm. Curve (b) shows the combined residual level and curve (d) shows the free residual level that would typically correspond to an initial ammonia concentration of 11 ppm in the area before and after breakpoint.

As indicated previously, the most obvious answer to controlling the process would be to use conventional feedback control based on free chlorine residual, inasmuch as the breakpoint and optimum ammonia destruction are characterized by the first appearance of a free residual. But to utilize this approach, an analytical method must exist that will accurately measure free chlorine in the presence of a rather large combined residual. And should only combined chlorine residual be present, the continuous analyzer must then indicate that no free chlorine is present, which means that the breakpoint has not yet been reached.

The problem with using feedback control based on a standard free chlorine residual analyzer will now be illustrated by the following example:

If the ammonia present in the water were initially 10 ppm, and a 3 ppm free chlorine residual were picked as the control point, a dose of 79 ppm of chlorine would put the process past breakpoint and the analyzer could be set to read 3 ppm. Should the ammonia level thereafter drop, this would create no problem, for then the analyzer would sense the increase in free chlorine residual and cut back on the chlorination to re-establish a 3 ppm level of free chlorine residual.

But if from an initial level of 10 ppm, the ammonia level were to rise, say, to 11 ppm, the same 79 ppm dosage of chlorine would push the process to the left of breakpoint, as shown in curve (b) in FIG. 2. Under these conditions, no free chlorine exists, and 10 ppm combined chlorine is present. If, in the presence of this 10 ppm combined chlorine, the analyzer possesses a combined chlorine error and indicates an apparent free chlorine residual of 4 ppm, the analyzer will instruct the chlorinator to throttle down. In doing so, the apparent error would increase, and the process would rapidly go out of control.

Thus the need is for an instrument to measure free chlorine residual to the exclusion of a combined chlorine error in order properly to control the breakpoint chlorination process.

Referring now to FIGS. 3 and 4, an amperometric analyzer is shown in accordance with the invention, which is adapted to measure free chlorine residual to the practical exclusion of a combined chlorine error. The analyzer incorporates an electrode cell of a known type, such as that included in the Residual Chlorine Analyzer Model 17B3200 manufactured and sold by Fischer & Porter Company of Warminster, Pennsylvania, and described in their Instruction Bulletin 17B3200.

In the amperometric analyzer, a sample stream of liquid whose chlorine content is to be analyzed, is caused to flow at a controlled rate through an inlet tube 10 into the bottom of the cell, and from there through the annular region between a centrally-disposed measuring electrode 11 and a cylindrical counter electrode 12 concentric therewith. The liquid then overflows into an outlet tube 13 which carries the liquid to a drain.

Measuring electrode 11 is mechanically and electrically connected to the shaft of a motor 14 disposed thereabove. Motor 14 serves to rotate the measuring electrode at high speed (i.e., 1500 rpm) to facilitate the maintenance of ideal reproducible electrolytic conditions and to render the output of the cell independent of slight variations in sample flow rate.

A spring-loaded brush 15 at the top end of the motor serves to connect the rotating electrode assembly to the measuring circuit. The stationary counter electrode is connected to the measuring circuit by means of an electrical pin connector 16 that protrudes through the electrode housing.

When a cell of this type is used in the conventional manner for residual chlorine analysis, as in the case of Model 17B3200 mentioned previously, the cell is operated in the galvanic mode, in which event the cell must employ electrodes of dissimilar material. Thus in Model 17B3200, the measuring electrode is formed of gold of high purity, and the counter electrode is made of pure copper. In the galvanic mode, the cell functions like an ordinary wet-cell battery, except that the current generated therein varies as a function of changes in the chlorine content of the sample stream.

In the present invention, the cell is caused to operate in an impressed-potential mode. This is accomplished by means of an external voltage source 17 connected in series with the electrodes and a load resistor 18, across which an output signal is developed. The signal appears at terminals 19 which may be connected to a suitable indicator calibrated in units of free chlorine residual, a recorder, or to a chlorinator control system. In practice, as with Analyzer Model 17B3200, a thermistor responsive to the temperature of the sample stream, may be shunted across the output terminals to compensate for changes in temperature.

Inasmuch as a galvanic action is not required, a cell of the present type may employ measuring and counter-electrodes of like material as well as electrodes of different material, such as gold and copper. Inasmuch as a cell operating in the impressed-potential mode will be compared hereinafter with one functioning in the galvanic mode, we shall first consider the nature of galvanic mode operation.

When water is present in a galvanic-mode cell, the measuring electrode becomes negatively charged or polarized, whereas the counter electrode acquires a positive charge due to the relative positions of the electrode metals in the electromotive series. The abundance of electrons in the measuring electrode prevents more electrons from flowing to it, so that no current flows in the circuit when chlorine is absent.

However, when chlorine is present in the sample stream flowing through the galvanic-mode cell, the chlorine acts to partially de-polarize the measuring electrode, thereby allowing more electrons to flow to it and causing current flow in the external circuit. The reaction at the measuring electrode may be represented in simplified form as:

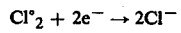

The symbol "$e^-$" represents electron flow from the counter electrode where simultaneously copper is being oxidized to form cupric ions:

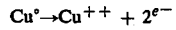

In effect, the chlorine depolarizes the measuring electrode, allowing copper to go into solution at the counter electrode as electrons flow in the external circuit to replenish the polarizing layer at the surface of the measuring electrode. The depolarizing current passing through the load resistor causes a potential drop thereacross which is measured by a suitable indicator calibrated in units of chlorine concentration.

In the present invention, wherein the measuring electrode operates with an impressed potential, the appropriate level for this potential to effect accurate measurement of chlorine content can be obtained by determining the current-voltage relationship of the cell in conjunction with a third or reference electrode 20 in a test circuit, as shown in FIG. 5.

It will be seen that cell electrodes 11 and 12 are connected in series with an ammeter 21 and an external voltage source 17A, whose voltage level is adjustable by a potentiometer or similar means. The potential established between reference electrode 20 and measuring electrode 11 is indicated by a voltmeter 22 which is of the high-impedance type.

The magnitude of voltage source 17A is varied throughout a predetermined range, and in the course thereof the corresponding current is observed on ammeter 21 while monitoring the voltage reading on voltmeter 22. A typical current-voltage curve resulting from this test procedure is shown in FIG. 6.

In FIG. 6, it will be seen that the current in the measuring electrode - counter electrode circuit increases progressively as the voltage between the measuring electrode and the reference electrode becomes more negative, until a plateau is reached represented by the shaded area (S). In this plateau, a further increase in voltage has little influence on current flow. The plateau reflects the well-known limiting current, where the electro-chemical reaction of interest, is diffusion-controlled. Under these conditions, the cell will be linear with respect to the chlorine concentration of the sample being measured.

Having established the current-voltage relationship for the test solution, the impressed voltage source can be removed and the potential of the measuring electrode can be measured relative to the reference electrode. If it falls into the plateau area by virtue of the galvanic action or if the use of a different counter electrode material will cause it to fall into this region, a galvanic-type cell will result. Otherwise, a fixed impressed potential can be added to cause the measuring electrode to assume the proper value.

Free chlorine can be measured with a gold/copper galvanic-type amperometric cell, either directly as the hypochlorous-acid species, or its operation can be improved by first adding excess potassium bromide (KBr) to the sample solution, and then measuring the equivalent bromine liberated, in the manner described in Morrow U.S. Pat. No. 3,413,199.

Normally, when free chlorine is measured in a water sample, chloramines are present in very small quantities relative to the free chlorine, and their interference with the measurement is insignificant and may therefore be ignored. But when the breakpoint chlorination technique is used for ammonia removal in sewage, significant quantities of chloramines can co-exist with free chlorine even though the breakpoint has been exceeded. Moreover, chloramines can be present at very high levels prior to breakpoint. It is vital, therefore, that the analyzer operating for the purpose of identifying free chlorine, does not falsely indicate an apparent free residual because of chlorine interference.

FIG. 7 shows a group of current-voltage curves that are important in understanding the gist of the present invention. Curve (1) represents the response of a gold/copper electrode couple for a solution of 8 ppm of free chlorine (only) that has been adjusted to pH 4 with a suitable buffer that maintains the proper electrolytic conditions of the amperometric cell, regardless of the natural alkalinity of the water supply.

The potential of the measuring electrode was compared to a reference electrode SCE (saturated calomel electrode) at various applied potentials. It will be seen in curve (1), that the limiting current region falls between + 0.05 to − 0.40 volts vs. SCE.

In Curve (2), the same 8 ppm free chlorine was treated with excess KBr in the buffer, to convert the chlorine to bromine. The bromine is characterized by having a longer plateau region between about + 0.40 and − 0.35 volts vs. SCE.

Curve (3) is produced when 8 ppm of chloramine (only) is measured at pH4, with either KBr present or absent in the buffer. It is obvious that no bromine is liberated by chloramines at pH4, or else that the bromine wave would appear at a characteristically more positive value. Curve (4) results from a solution that contains no chlorine in any form. The sharp rise of current which begins at about −0.015 volts, is due to dissolved oxygen.

If the applied potential is removed from the circuit, so that the potential developed by the measuring electrode ME is due solely to the galvanic action of the gold/copper couple, the measured ME voltage compared to SCE for solutions containing only free chlorine, is as follows:

(a) Without KBr in buffer — ME vs. SCE = −0.02 volts
(b) With KBR in buffer — ME vs. SCE = + 0.10 volts From the curves in FIG. 7, it becomes evident that if significant quantities of chloramine are not present in the sample being tested, a gold/copper or other form of galvanic cell, with or without KBr additive in the buffer, can be utilized to provide accurate reading of free chlorine. When, however, substantial levels of chloramine co-exist with free chlorine or exist in the absence of free chlorine, a cell operating in the galvanic mode will produce a spurious reading in which the chloramine shows up as an apparent free chlorine.

By operating the gold/copper cell in the impressed-potential mode in the circuit arrangement illustrated in FIG. 4, the measuring electrode can be set to operate at + 0.40 volts vs. SCE. At this impressed-potential level, free chlorine can be measured with essentially no chloramine error. Thus, in FIG. 8, the apparent free chlorine residual (ppm 0 to 20), is indicated at various concentrations (ppm 0 to 120) of chloramine present in a sample that contains no free chlorine.

Curve (1) in FIG. 8 shows the response of a cell operating in the galvanic mode, to the various levels of chloramine present. It will be obvious from curve (1) that under these conditions, serious apparent free chlorine levels are indicated. Curve (2) in FIG. 8 shows the response of a cell operating in the impressed-potential mode, in which the measuring electrode is caused to assume a potential of +0.40 volts vs. SCE. It will be seen that even for very high levels of chloramine, very little apparent free chlorine is indicated by the cell.

The dashed-line curve (3) in FIG. 8 shows the response of either the galvanic mode or the impressed-potential mode cell when free chlorine instead of chloramine is plotted along the X-axis. It will be seen that in these instances the free chlorine indications rise sharply as the level of free chlorine increases.

Thus, by setting the impressed potential at a current-limiting level, the amperometric cell will afford an accurate reading of free chlorine residual even when substantial quantities of combined chlorine are present because of the presence of ammonia in the water being chlorinated, for the impressed potential cell is insensitive to combined chlorine residual.

It then becomes possible, as shown in FIG. 9, using a breakpoint chlorination technique, to employ a feedback-control system CS responsive to the breakpoint signal produced by the impressed-potential cell analyzer AN, to accurately govern the dosage applied by chlorinator CH to effect the destruction of ammonia in the water supply line L.

While there has been shown and described a preferred embodiment of residual chlorine analyzer in accordance with the invention, it will be appreciated that many changes and modifications may be made therein without, however, departing from the essential spirit thereof.

I claim:
1. The method of measuring the free chlorine residual in a chlorinated liquid supply having an ammonia con- tent giving rise to a combined chlorine residual, said liquid supply being chlorinated by a controllable chlorinator, said method comprising the steps of:

A. feeding a sample stream of said supply which is buffered and contains a potassium bromide additive through a passage defined by the space between the measuring electrode formed of gold and the counter electrode formed of copper of an amperometric cell, B. impressing across said electrodes a potential at a current-limiting level at which the current flow in the cell as a result of chlorine content increases progressively as a function of the free chlorine residual in the sample stream and is substantially insensitive to the combined chlorine residual therein, C. measuring said current to indicate the first appearance of said free chlorine residual and, D. controlling the operation of said chlorinator in response to the indication of the first appearance of the chlorine residual so that the degree of chlorination is such as to maintain a breakpoint condition at which ammonia destruction is optimized.

2. The method as set forth in claim 1, further including the step of controlling the rate of flow of the sample stream fed into said passage.

* * * * *